(12) United States Patent
Gaffney et al.

(10) Patent No.: US 11,589,893 B2
(45) Date of Patent: Feb. 28, 2023

(54) MEDICAL DEVICE AND RELATED METHODS

(71) Applicant: Boston Scientific Scimed, Inc., Maple Grove, MN (US)

(72) Inventors: Brian Gaffney, Rutland, MA (US); Samuel Raybin, San Jose, CA (US); Paul Smith, Smithfield, RI (US); Ray Tong, Foxboro, MA (US); Naroun Suon, Lawrence, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 315 days.

(21) Appl. No.: 16/801,745

(22) Filed: Feb. 26, 2020

(65) Prior Publication Data
US 2020/0187974 A1    Jun. 18, 2020

Related U.S. Application Data

(63) Continuation of application No. 15/240,698, filed on Aug. 18, 2016, now Pat. No. 10,610,254.
(Continued)

(51) Int. Cl.
| | | |
|---|---|---|
| *A61B 17/3205* | (2006.01) | |
| *A61B 17/32* | (2006.01) | |
| *A61B 18/14* | (2006.01) | |
| *A61B 17/221* | (2006.01) | |
| *A61B 17/00* | (2006.01) | |

(52) U.S. Cl.
CPC .. *A61B 17/32056* (2013.01); *A61B 17/32002* (2013.01); *A61B 17/320016* (2013.01); *A61B 2017/00269* (2013.01); *A61B 2017/00296* (2013.01); *A61B 2017/00358* (2013.01); *A61B 2017/00818* (2013.01);
(Continued)

(58) Field of Classification Search
CPC ...... A61B 2017/2212; A61B 17/32056; A61B 17/32002; A61B 2017/00358; A61B 2018/141; A61B 17/221–2017/2217; A61B 2018/1407–141; A61B 17/2909–2017/2925; A61B 17/2841–2017/2845; A61B 2017/00269; A61B 2017/32006; A61B 17/320016–32002; A61B 2017/320028–00358; A61B 17/26
See application file for complete search history.

(56) References Cited

U.S. PATENT DOCUMENTS

| | | |
|---|---|---|
| 4,326,530 A | 4/1982 | Fleury, Jr. |
| 4,493,320 A | 1/1985 | Treat |

(Continued)

OTHER PUBLICATIONS

U.S. Appl. No. 15/050,036, filed Feb. 22, 2016 (45 pages).
International Search Report and Written Opinion issued in PCT/US2016/047792, dated Dec. 19, 2016 (15 pages).

*Primary Examiner* — Timothy J Neal
*Assistant Examiner* — Brigid K Byrd
(74) *Attorney, Agent, or Firm* — Bookoff McAndrews, PLLC

(57) ABSTRACT

Exemplary medical devices may include a snare device. The snare device may include a first leg having a proximalmost end and a second leg having a proximalmost end. The first leg and the second leg may form a distal loop. The proximalmost end of first leg may be independently moveable relative to the proximalmost end of the second leg.

20 Claims, 10 Drawing Sheets

Related U.S. Application Data

(60) Provisional application No. 62/207,789, filed on Aug. 20, 2015.

(52) U.S. Cl.
CPC ............... *A61B 2017/2212* (2013.01); *A61B 2017/32006* (2013.01); *A61B 2018/141* (2013.01)

(56) References Cited

U.S. PATENT DOCUMENTS

| | | | |
|---|---|---|---|
| 4,718,419 A | | 1/1988 | Okada |
| 5,163,942 A | * | 11/1992 | Rydell ............ A61B 17/32056 606/1 |
| 5,201,741 A | | 4/1993 | Dulebohn |
| 5,254,088 A | * | 10/1993 | Lundquist ......... A61M 25/0136 604/95.04 |
| 5,836,947 A | * | 11/1998 | Fleischman ............ A61N 1/056 606/41 |
| 6,224,611 B1 | | 5/2001 | Ouchi |
| 6,258,101 B1 | * | 7/2001 | Blake, III ............ A61B 17/221 606/113 |
| 8,211,114 B2 | | 7/2012 | Nobis et al. |
| 2003/0109889 A1 | * | 6/2003 | Mercereau ........... A61B 17/221 606/127 |
| 2003/0236519 A1 | * | 12/2003 | Kear .................... A61B 1/0052 606/41 |
| 2004/0092953 A1 | | 5/2004 | Salameh et al. |
| 2004/0199200 A1 | | 10/2004 | Teague |
| 2007/0250012 A1 | | 10/2007 | Lu et al. |
| 2010/0204710 A1 | | 8/2010 | Shaw et al. |
| 2012/0172662 A1 | | 7/2012 | Kappel et al. |
| 2012/0172864 A1 | | 7/2012 | Farin et al. |
| 2013/0184739 A1 | | 7/2013 | Brady |
| 2015/0105789 A1 | | 4/2015 | Raybin et al. |

* cited by examiner

MEDICAL DEVICE AND RELATED METHODS

CROSS-REFERENCE TO RELATED APPLICATIONS

This application is a continuation of U.S. application Ser. No. 15/240,698, filed on Aug. 18, 2016, which claims the benefits of priority from U.S. Provisional Application No. 62/207,789 filed on Aug. 20, 2015, the entireties of each of which are incorporated herein by reference.

TECHNICAL FIELD

Embodiments of the present disclosure relate generally to medical devices for grasping, cutting, or otherwise manipulating tissue. In particular, embodiments of the present disclosure relate to snare devices and related methods of use.

BACKGROUND

A wide variety of medical techniques and instruments have been developed for diagnosis and/or treatment within a patient's body, such as within a patient's Gastrointestinal (GI) tract. Endoscopic Mucosal Resection (EMR), Endoscopic Sub-mucosal Resection (ESR), Polypectomy, Mucosectomy, etc., are minimally invasive treatment methods for both malignant and non-malignant lesions. Endoscopic medical procedures, such as, for example, EMR, may be used to excise sessile adenomas or other unwanted tissue (i.e., tumors attached to a bodily surface) from the surface of an anatomical lumen. Such procedures often require the resection of one tissue plane while leaving an underlying tissue plane intact. Commonly, snares are used during such medical procedures, for resecting tissue from a target site. However, many conventional snares operate in only one degree of freedom, and manipulation of the snare is dependent on the tip deflection of an endoscope or other device used for insertion into the patient. Further, the pre-formed shape of the wire typically determines the shape of the snare within the patient. Thus, the ability to form a variety of different shapes, and the control and functionality of conventional snares, may be limited.

Further, conventional snares typically move in a distal and proximal direction, with limited ability to deflect to a side. After conventional snares are positioned in a "loop" over the target tissue, snares are then drawn in the proximal direction to tighten the loop. Drawing the snare in the proximal direction, however, can cause the snare to slip off the target tissue. Further, when using this conventional method, the ability to sever the target tissue from the patient's body may be limited to the sharpness of the interior of the snare and the pressure applied.

SUMMARY

Embodiments of the present disclosure relate to, among other things, snare devices. Each of the embodiments disclosed herein may include one or more of the features described in connection with any of the other disclosed embodiments.

According to one aspect of the present disclosure, a medical device may include a first leg having a proximalmost end; and a second leg having a proximalmost end. The first leg and the second leg may form a distal loop, and the proximalmost end of first leg may be independently moveable relative to the proximalmost end of the second leg.

Additionally or alternatively, the medical device may include one or more other features describe here. Examples of the snare device may additionally and/or alternatively include one or more other features. For example, at least a portion of a surface facing an interior of the distal loop of at least one of the first leg and the second leg may include a plurality of teeth. In another example, the first leg and the second leg may include a plurality of segments, wherein a flexibility of at least one of the plurality of segments may be different than a flexibility of an adjacent segment. In another example, the plurality of segments may consist of only one wire. A first segment of the plurality of segments may include a first wire, and a second segment of the plurality of segments may include a second wire. A cross-sectional thickness of a first segment of the plurality of segments may be different than a cross-sectional thickness of a second segment of the plurality of segments. At least one actuation mechanism may be configured to move at least one of the proximalmost end of the first leg and the proximalmost end of the second leg. The at least one actuation mechanism may include one of a knob, a lever, a screw, and a rotation wheel.

According to another aspect of the present disclosure, a medical device may include a first leg having a proximal end, a second leg having a proximal end, wherein the first leg and the second leg form a distal loop, a rotatable handle portion coupled to the proximal end of the first leg and the proximal end of the second leg, and a stationary handle portion, wherein the rotatable handle portion is rotatable about a perpendicular axis to a longitudinal axis of the stationary handle portion.

Additionally or alternatively, the medical device may include one or more other features describe here. For example, the rotatable handle portion may be configured to move at least one of the proximal end of the first leg and the proximal end of the second leg. The rotatable handle portion may include a pulley, and the proximal end of the first leg and the proximal end of the second leg may be connected to form a continuous proximal loop around the pulley. The medical device may include a motor configured to rotate the pulley. The rotatable handle portion may include a rotation wheel and the proximal end of the first leg, and the proximal end of the second leg may be fixedly attached to the rotation wheel. The rotatable handle portion may be configured to move the distal loop in one or both of a clockwise direction or a counterclockwise direction. The rotatable handle portion may be configured to alternate between clockwise movement and counterclockwise movement of the distal loop.

According to another aspect of the present disclosure, a method for resecting tissue. The method may include inserting a snare into a body, wherein the snare includes a first leg with a proximalmost end and a second leg with a proximalmost end, wherein the first leg and the second leg form a distal loop, grasping tissue with the distal loop, moving the proximalmost end of the first leg relative to the proximalmost end of the second leg in a first direction, and thereafter moving the proximalmost end of the first leg relative to the proximalmost end of the second leg in a second direction, opposite the first direction.

Additionally or alternatively, the method may include one or more other features describe here. For example, at least a portion of a surface of at least one of the first leg and the second leg may include a plurality of teeth, the surface facing an interior of the distal loop. The plurality of teeth may resect the tissue. The method may include repeating the steps of moving the proximalmost end of the first leg relative to the proximalmost end of the second leg in the first direction, and thereafter moving the proximalmost end of the second leg in the second direction. The method may include after the repeating the steps, pulling the distal loop proximally.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description serve to explain the principles of the disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient. When used herein, the term "approximately" may indicate a range of values within +/−5% of a stated value.

The present disclosure is drawn to various embodiments of snare devices. A distal loop may be located at a distal end of the snare device. In general, upon locating tissue which is to be removed and positioning the snare proximate the tissue, one or both of the proximal ends of the snare device may be pushed in the distal direction so that the snare is ejected from the distal end of a sheath and/or endoscopic device. The snare and/or the endoscopic device may be manipulated from outside of the patient to pass the loop over tissue. Unlike conventional snares, however, the shape of the distal loop of the present disclosure may be changed to match the shape of a lesion by exposing and/or extending different areas of the snare device to change the geometry of the distal loop. The geometry of the distal loop may be changed by certain segments of the snare device having different flexibilities cross-sectional shapes or thicknesses, or materials; the ability of the proximal ends of the snare device to move independently of each other; or a combination thereof. Additionally, multiple geometries of the snare loop, e.g., hexagonal, duckbill, round, oval, etc., may be incorporated into a single snare device.

Further, unlike conventional snares, the manipulation of the snare device and/or the distal loop of the present disclosure may not be solely dependent on the tip deflection of a delivery device (e.g., an endoscope, sheath, catheter, etc.). The snare device of embodiments of the present disclosure may provide the operator more control than conventional snares. For example, both proximal ends of the snare device may be manipulated independently of each other. The geometry of the distal loop may, therefore, be manipulated so that the distal loop moves side to side as opposed to just in and out (proximal and distal) like traditional snares.

In addition, while conventional snares resect the target tissue by drawing the snare device and/or distal loop in the proximal direction to tighten the distal loop around a base region or neck of the tissue, devices and methods according to certain embodiments described herein may be used to "saw" tissue, by alternately pushing and pulling on the proximal ends of the snare device.

Exemplary Embodiments

Figure 1:
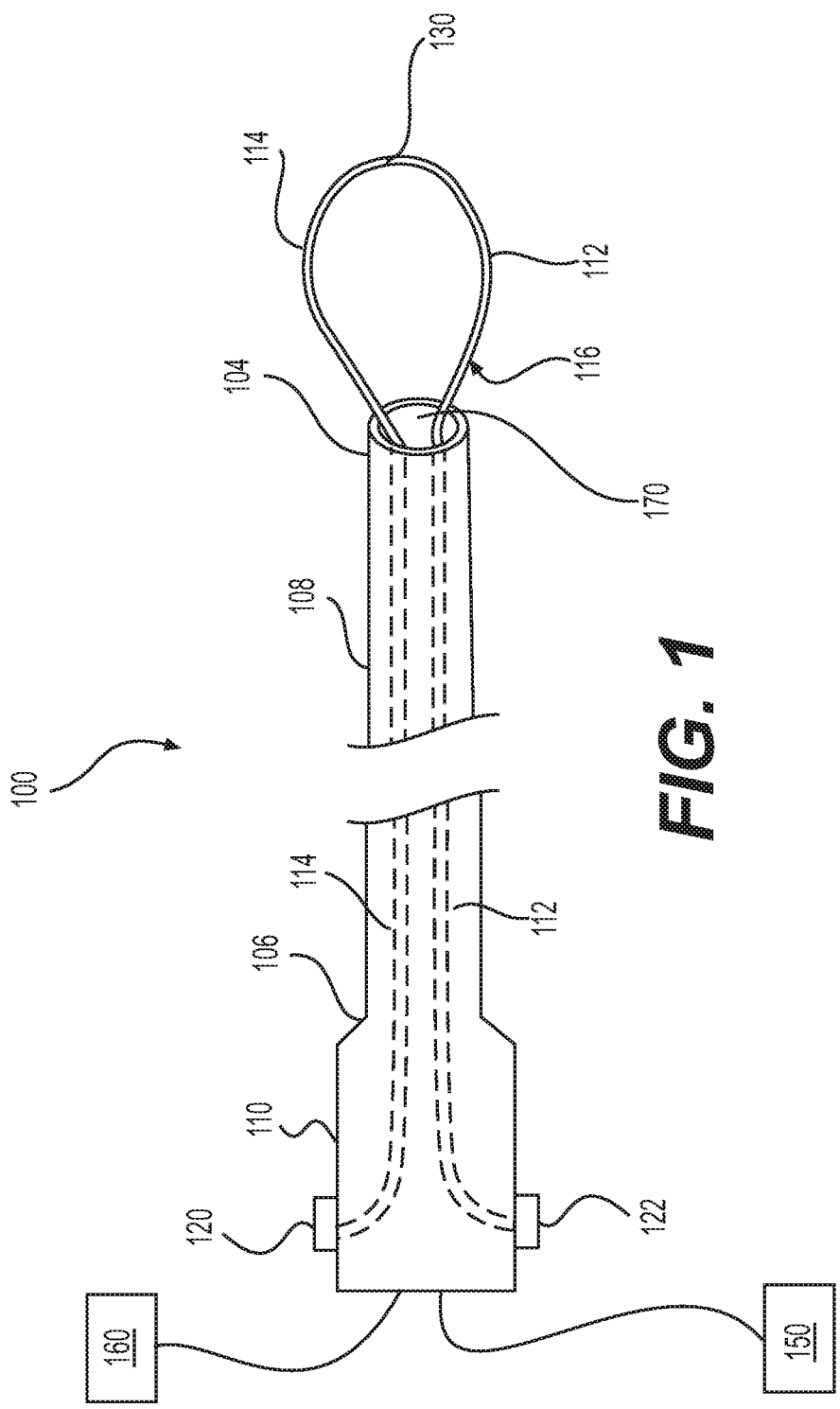
FIG. 1 illustrates an example of a medical device including a handle, a sheath, and a snare in an extended position.

FIG. 1 illustrates an exemplary medical device 100 for grasping, resecting or otherwise manipulating tissue. In some examples, device 100 may extend through a lumen of an endoscopic device. An endoscopic device (for example, an endoscope, colonoscope, sheath, catheter, or other device) may be inserted into an internal cavity of a patient, e.g., into the colon, the esophagus, or other portion of the GI tract, and may be used to locate tissue of interest, including abnormal tissue growths, such as a polyp, in the internal cavity. The device 100 may include a hollow, flexible, elongate sheath 108. Sheath 108 may have a distal end 104 and a proximal end 106 with a lumen 170 therebetween. Proximal end 106 may be coupled to or otherwise integral with a handle portion 110, while distal end 104 may remain open. Snare device 116 may be slidably disposed within lumen 170 and may be extended distally from distal end 104 of sheath 108.

In one example, medical device 100 may attach to or include a motor 150 and/or an electrical source 160. Motor 150 may be, for example, a DC motor configured to actuate the proximalmost ends of snare device 116. Alternatively, the ends of snare device 116 may be actuated by any other suitable device capable of pushing/pulling on the proximal ends of snare device 116, including manually operated actuators. Electrical source 160 may provide electricity. For example, snare device 116 may be used for electrocautery and electrical source 160 may provide current to the snare device 116. In some implementations, medical device 100 may include other components, including imaging, irrigation, and aspiration capabilities.

I. Snare Device

Once sheath 108 is positioned within the patient's body, an operator may move snare device 116 between an extended state (FIG. 1) and a retracted state (not shown). Snare device 116 may include a distal loop defined by a first side or leg 112, a second side or leg 114 connected to the first side 112 at a distal tip, and an open proximal end, where the sides/legs are unconnected. In the retracted state, the distal loop disposed on the distal end of snare device 116 may be in a collapsed configuration to fit within lumen 170 of sheath 108. In the extended state, a portion of snare device 116 including the distal loop may extend distally out of the distal end 104 of sheath 108, and a portion of first side 112 and second side 114 (extending proximally from the distal loop) may be disposed within lumen 170. The diameter of the loop in the extended state may be between approximately 5 mm and approximately 40 mm, or between approximately 10 mm and approximately 34 mm.

Snare device 116 may be formed in any way, of any material, and/or with any number of segments/wires. For example, snare device 116 may be a single, continuous monofilament piece of material, such as a wire, forming a loop. Alternatively, snare device 116 may include a plurality of segments. In the example shown in FIG. 1, snare device 116 may be two wires connected at a distal end at connection point 130 by any suitable connection, including crimping, welding, brazing, soldering, etc.

Snare device 116 may include coated wires. For example, some or all of snare device 116 may be coated, for example, by duraskin, a PTFE "Teflon" based material. Such a coating may allow for both sides 112 and 114 of snare device 116 to be disposed and slidably move within a single lumen, e.g. lumen 170 of sheath 108. Such a coating may also provide electrical insulation.

In some examples, snare device 116 may be formed from stainless steel, nitinol, and/or other biocompatible material. Snare device 116 may include multiple loops. Snare device 116 may include any cutting and cautery functionality suitable for the desired implementation. For example, snare device 116 may be a hot snare (capable of conducting electrocautery current) or a cold snare (incapable of conducting current).

Snare device 116 and/or device 100 may be configured in a variety of ways to produce a variety of distal loop geometries and/or provide multiple degrees of freedom. For example, multiple distal loop geometries, including, e.g., hexagonal, duckbill, round, oval, may be produced by manipulating a single snare device 116. The techniques and features described herein may produce geometries and/or degrees or freedom not achievable with conventional snare loops.

A. Snare Loop with Varying Flexibility

In some examples, a variety techniques and/or wire configurations may be used to produce additional distal loop geometries. For example, snare device 116 may include different flexibilities at different locations and along different segments. The different flexibilities may be due to, for example, different wire thicknesses, materials, and/or cross-sectional shapes, and/or features cut into or otherwise present in the wire or segments thereof.

Different thicknesses at certain segments along snare device 116 may affect that segment's ability to bend and ease of bend. For example, segments where the wire has a thinner cross-sectional thickness may bend more (and/or bend as a result of less pressure). Segments in which the wire has a thicker cross-sectional thickness will remain straighter and/or require additional pressure to bend. Snare device 116 may have different thicknesses by, for example, forming snare device 116 of a plurality of connected wires, each with different thickness. Additionally or alternatively, segments of snare device 116 may include different thicknesses by forming a single wire with different thicknesses or milled to different thicknesses. The segments may gradually change thicknesses and/or the segments may distinctly transition (e.g., incremental change) between thicknesses.

Figure 2:
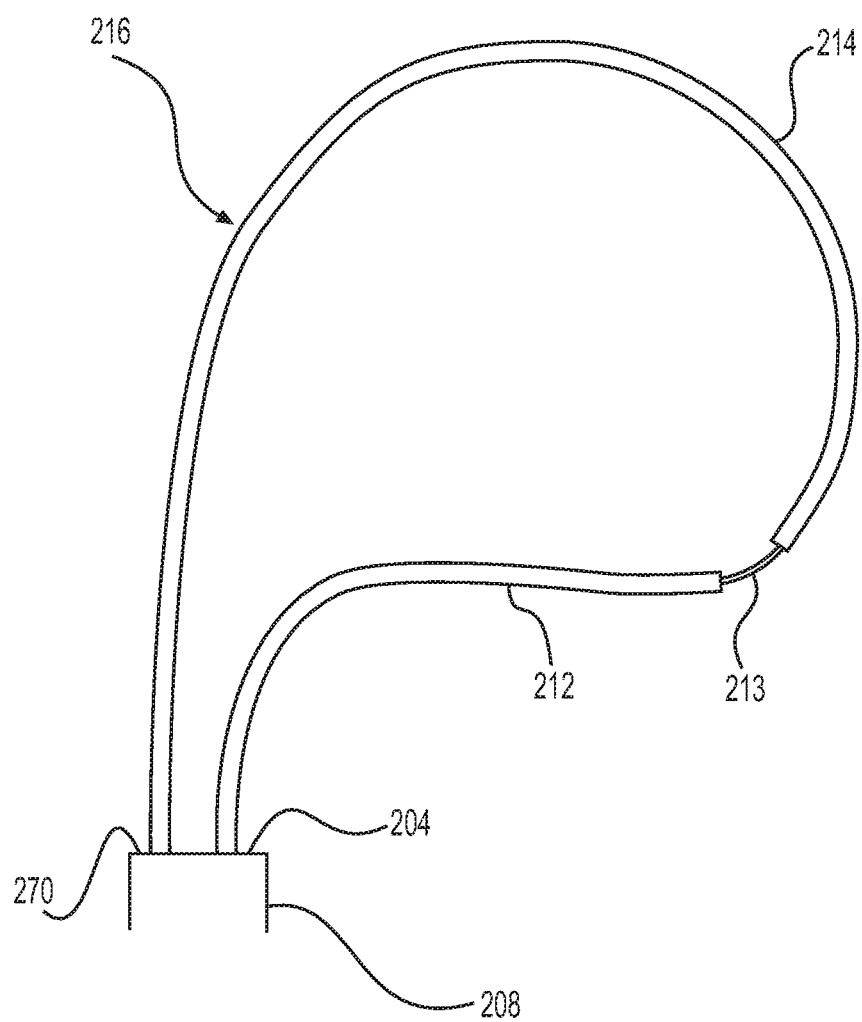
FIG. 2 illustrates an example of a snare with a plurality of segments having different thicknesses.

In the example illustrated in FIG. 2, snare 216 (extending from distal end 204 of sheath 208) includes at least three segments, e.g., first segment 212, second segment 213, and third segment 214. As shown in FIG. 2, the wire of second segment 213, disposed between and connected to segments 212 and 214, has a smaller cross-sectional thickness than segments 212 and 214. FIG. 2 illustrates an incremental change (or stepped change) in thickness (as opposed to a gradual change in thickness) between first segment 212 and second segment 213 and between second segment 213 and third segment 214. In some examples, the thicknesses of the segments may be between approximately 0.05 mm and approximately 1.5 mm in diameter, or between approximately 0.1 mm and approximately 1.0 mm in diameter.

Different material in different segments of snare device 116 may affect the flexibility of these segments. For example, a first material may be used for a first wire, and a second material may be used for a second wire. The first and second wires may then be connected to each other, for example, at connection point 130. The first material may be softer than the second material. In such an example, the first wire will bend more and/or may bend as a result of less pressure. The second wire may be straight and/or require additional pressure in order to bend.

In some examples, features may be cut into the wire to produce certain geometries. For example, slots at varying distances may be cut into the wire(s) of snare device 116. The closer the slots, the more flexible the wire. The further the slots are spaced from each other, the stiffer the wire. Segments of wire without slots will be even stiffer, remaining straighter and requiring additional pressure in order to bend.

In some examples, teeth may be cut and/or formed in the wire(s) of snare device 116. Snare device 316 of FIGS. 3A-D includes teeth 340 on the interior of the distal loop (the surface of the distal loop facing the interior of the loop). Teeth may be included on the full snare device 316 extending to the proximal end of the wire(s). Alternatively, teeth may be on only certain segments of snare device 316. For example, teeth may be included on the distal loop and/or only segments of the wire(s) configured to extend out of the sheath 308. In other examples, teeth may be included only on proximally-facing segments of the distal loop. In some example, teeth may be ground in the center of the distal loop and/or snare device, e.g., the midpoint of the snare device. In some examples, the segment of the snare device with teeth may have a length of approximately 5 cm to approximately 15 cm, or approximately 13 cm.

In addition to affecting the flexibility of the wire(s) and/or segments of the wire(s), teeth in the wire of the snare loop may provide for better traction on the target tissue. Teeth may provide the ability to saw cut the target tissue by actuating the proximalmost ends of sides/legs 312 and 314 of snare device 316 (as described in more detail below).

The geometry of the distal loop of snare device 116 also may be influenced by, for example, heating metals or superelastic metals on the full snare device and/or segments of the snare device. The wire(s) may be heat set to any desired shape by, e.g., using a mold and heat bath.

Snare device 116 may include any number of segments. Any of the above techniques for affecting flexibility and/or altering snare/distal loop geometries may be used alone or in combination.

B. Snare Loop with Independently Moveable Ends

In some examples, the snare device 116 may allow for a variety of distal loop geometries. These geometries may be created when the two proximal ends of the snare device 116 are manipulated a certain way by the operator. In some examples, various geometries may be created based on how the snare device is pushed out of the sheath and into the patient's body. For example, both proximal ends of the snare device 116 (e.g., the proximal end of side/leg 112 and the proximal end of side/leg 114) may be pushed an approximately equal distance and/or at approximately the same time. In some examples, one proximal end is push before, faster, farther, or harder than the other proximal end. One of the multiple available geometries may be chosen/created upon insertion into the patient (e.g., while exiting from the sheath) and/or the geometry may be changed during use (e.g., after insertion into the patient).

In the example shown in FIG. 1, proximal ends of sides 112 and 114 may be moved independently of each other, e.g., the proximalmost ends of sides 112 and 114 may move relative to each other. In some examples, the proximalmost ends of sides 112 and 114 may extend to the operator, e.g., through handle 110. Both ends of snare device 116 may thus be manipulated to give the operator direct control over the geometry of the distal end (e.g., the distal loop) of snare device 116. The ends may be manipulated by any actuation mechanism (e.g., actuation mechanisms 120 and 122). Examples of actuation mechanisms that may be used in connection with device 100 are described in further detail below.

Figure 3B:
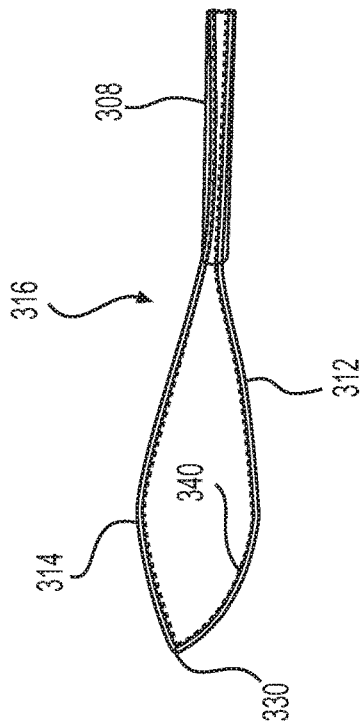
FIGS. 3A-3D illustrate examples of a snare in four different configurations.
Figure 3D:
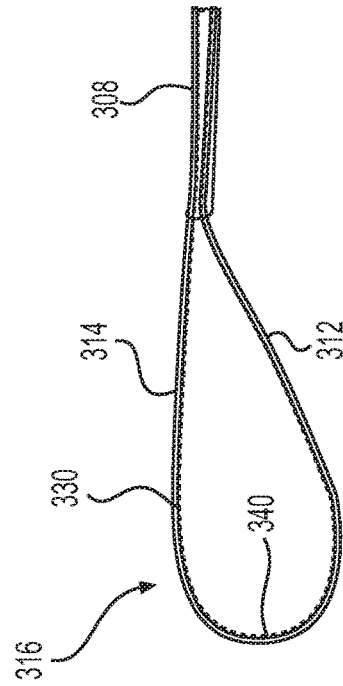
Figure 3A:
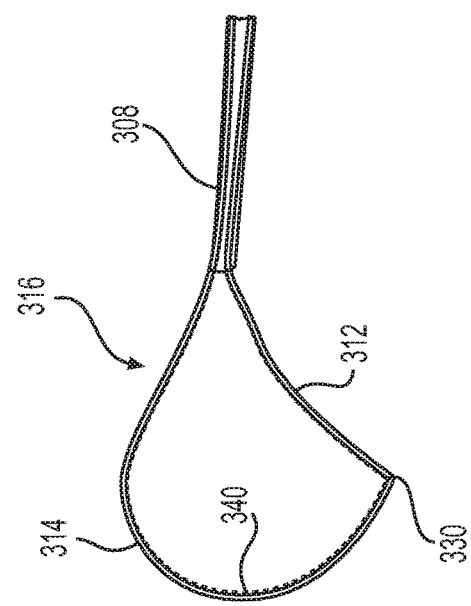
Figure 3C:
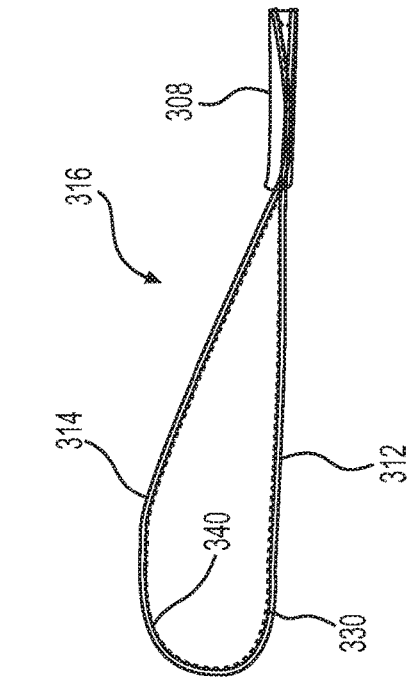

FIGS. 3A-D illustrate snare device 316 extending from the distal end of sheath 308. Snare device 316 includes sides 312 and 314 connected at connection point 330. Each of FIGS. 3A-D illustrate the snare device 316 with its proximalmost ends in different positions. For example, FIG. 3A illustrates an example in which the end attached to side 314 was pushed farther distally (e.g., in an extended position) than the end attached to side 312 (e.g., end of side 312 may be kept stationary or retracted while end of side 314 is moved distally). FIG. 3B illustrates an example in which both ends were pushed approximately the same amount by the operator (e.g., both ends are in an extended position by the same distance). FIG. 3C illustrates an example in which the end attached to side 314 was pushed farther distally (e.g., in an extended position) than the end attached to side 312 (e.g., in a stationary or retracted position). In the example shown in FIG. 3C, side 312 is positioned farther distally than in the example illustrated in FIG. 3A. FIG. 3D illustrates an example in which the end attached to side 312 was pushed farther distally (e.g. in an extended position) than the end attached to side 314.

I. Sheath

Sheath 108 may be circular, ovoidal, irregular, and/or any cross-sectional shape suitable to enter a body. Further, sheath 108 may have a uniform shape along its length, or may have a varying shape, such as a taper at the distal end to facilitate insertion within the body. Depending upon the particular implementation and intended use, the length of sheath 108 may vary. The diameter of sheath 108 may be tailored based on the body cavity and/or the delivery device (e.g., an endoscopic device). Similarly, depending upon the particular implementation and intended use, sheath 108 can be rigid along its entire length, flexible along a portion of its length, or configured for flexure at only certain specified locations.

Sheath 108 may be formed of any suitable material having sufficient flexibility to traverse body cavities and/or lumens of delivery devices. In general, sheath 108 may be made of any suitable material that is compatible with living tissue or a living system. That is, the sheath 108 may be non-toxic or non-injurious, and it should not cause immunological reaction or rejection. In some embodiments, sheath 108 may be made of polymetric elastomers, rubber tubing, and/or medically approved polyvinylchloride tubing. Polymeric elastomers may be, for example, EVA (Ethylene vinyl acetate), silicone, polyurethane, and/or C-Flex. Sheath 108 may be designed to impose minimum risk to the surrounding tissues and/or lumens of delivery devices while in use. To this end, one or more portions of sheath 108 may include atraumatic geometrical structures, such as rounded or beveled terminal ends or faces, to reduce trauma and irritation to surrounding tissues.

Further, the sheath 108 may include any suitable coating and/or covering. For example, the outer surface may include a layer of lubricous material to facilitate insertion through a body lumen or surgical insertion. Further, sheath 108 may be coated with a biocompatible material such as Teflon. To inhibit bacterial growth in the body cavity, sheath 108 may be coated with an antibacterial coating. Further, an anti-inflammatory substance may also be applied to the outer surface of the sheath 108, if required.

II. Handle

Handle portion 110 can be attached to sheath 108 by, for example, welding, a locking configuration, use of an adhesive, or integrally forming with sheath 108. Handle portion 110 may include a number of other structural features. The handle portion 110 may include one or more actuation mechanism (e.g., actuation mechanisms 120 and 122) to push/pull the proximal ends of the wires of snare device 116. Actuation mechanisms 120 and/or 122 may include levers, knobs, screws, or any other mechanism suitable for moving the proximalmost ends of side/leg 112 and side/leg 114 of snare 116. The proximalmost ends of snare 116 may be moved by actuation mechanism 120 and/or 122 any suitable distance, at any suitable speed, and/or with any suitable amount of force.

III. Exemplary Method

In some examples, a snare device may be used in a method where a sawing motion is used to resect target tissue. One exemplary method is described below. For example, a delivery device (e.g., an endoscopic device, such as, an endoscope, colonoscope, or other device) may be inserted into an internal cavity of a patient, e.g., into the colon, the esophagus, or other portion of the GI tract, and may be used to locate tissue of interest, including abnormal tissue growths, such as a polyp, in the internal cavity. Upon locating the target tissue, the proximalmost ends of snare device 116 may be pushed in the distal direction so that portions (e.g., the distal loop) of snare 116 are ejected from the distal end 104 of sheath 108 and/or the delivery device. Snare device 116 may be manipulated from outside the patient in any of the ways described above and/or any way known in the art in order to pass the distal loop of snare device 116 over the target tissue. One or both ends of snare 116 may then be drawn in the proximal direction to contact the interior facing surfaces of the loop against the target tissue and/or tighten the distal loop of snare 116 around the target tissue. Once the snare 116 contacts the target tissue, the operator may initiate a saw motion, drawing the interior surface of the snare back and forth across the target tissue. The operator may do so by alternately pushing and pulling on the two proximal ends of the tensioned wire, cutting through the tissue currently snared. For example, an operator may utilize actuation mechanism 120 to push snare side/leg 114 forward distally and, at the same time or thereafter, pull snare side/leg 114 back proximally. As shown in FIG. 1 when viewed from the handle of the device 100, the loop of the snare device 116 would then be drawn across the target tissue from the left of the figure to the right (e.g., clockwise). In some examples, the process may then be reversed so that snare side 112 may be pushed forward, thus alternating between a clockwise and counterclockwise motion across the target tissue. In some examples, such as those illustrated in FIGS. 3A-D, teeth 340 may be disposed on the interior-facing surface of snare device 316, and these teeth may be drawn across the target tissue. The sawing motion may be used in conjunction with electrocautery to provide more robust cutting. The sawing may continue until the target tissue is no longer attached to the patient. Once the desired resection is complete, snare device 116 may be retracted (e.g., by pulling actuation mechanism 120 and/or 122) into sheath 108. Sheath 108 may be retracted into the delivery device (e.g., endoscopic device) and the delivery device may be removed from the patient.

IV. Alternative Device

Figure 4:
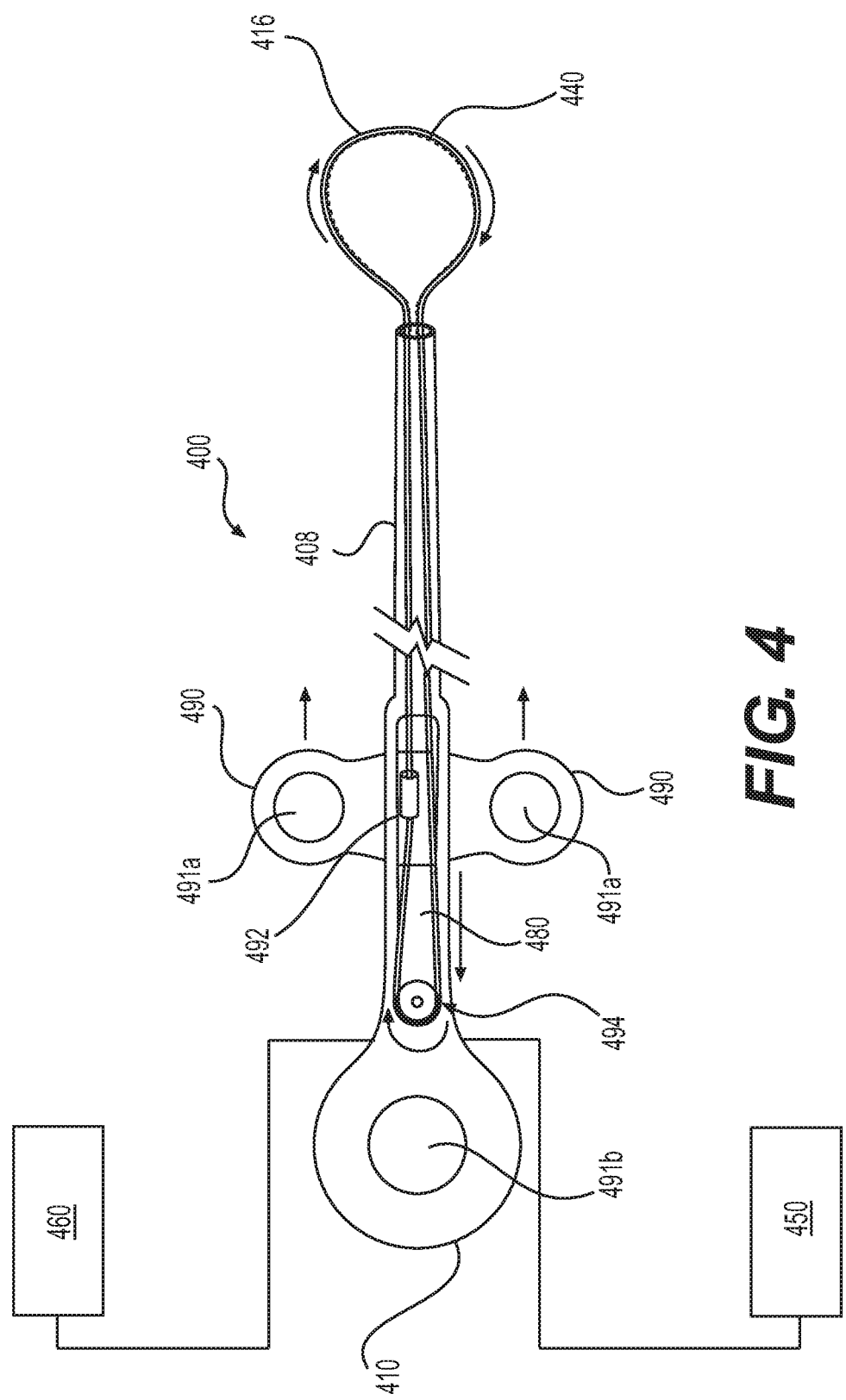
FIG. 4 illustrates an alternative exemplary medical device.

FIG. 4 illustrates an alternative exemplary medical device 400 including an alternative handle portion 410. The device 400 may include a hollow, flexible, elongate sheath 408. Sheath 408 may have a distal end and a proximal end with a lumen therebetween. The proximal end may be coupled to or otherwise integral with a handle portion 410, while distal end remains open. Snare device 416 may be slidably disposed within the lumen of sheath 408 and may extend distally from the distal end of sheath 408.

In one example, medical device 400 may attach to or include a motor 450 and/or an electrical source 460. Motor 450 may be, for example, a DC motor configured to actuate the proximalmost ends of snare device 416. Alternatively, the ends of the snare device 416 may be actuated by any other suitable device capable of pushing/pulling on the proximal ends of snare device 416, including manually operated actuators. Electrical source 460 may provide electricity. For example, snare device 416 may be used for electrocautery, and electrical source 460 may provide current to the snare device 416. In some implementations, medical device 400 may include other components, including imaging, irrigation, and aspiration capabilities.

Similar to snare devices 116, 216, and 316, snare device 416 may be a single continuous material or may include a plurality of connected segments. Snare device 416 may be configured so that when a sliding portion 490 of handle 410 is slid or positioned distally (as shown in FIG. 4), a portion of snare device 416 may extend distally from sheath 408, where it is in a position for capturing and removing polyps. When sliding portion 490 is slid or positioned proximally (not shown), snare device 416 may be substantially collapsed and disposed within sheath 408.

Handle 410 of FIG. 4 may include a number of other structural features. For example, one or more finger holes 491a may be within sliding portion 490 to assist movement of sliding portion 490, and a thumbhole may be within a proximal portion of handle 410. A crimp 492 may be disposed within and/or attached to handle 410, for example attached to sliding portion 490. Crimp 492 may connect the ends of snare 416 so that snare device 416 is one continuous loop.

Handle 410 may include a rotatable handle portion, e.g., pulley 494. The proximal end of snare device 416 may loop around pulley 494 and snare device 416 may ride over pulley 494. Pulley 494 may slide distally and proximally within a slot 480 of handle 410, so that pulley 494 moves with sliding portion 490. Rotation of pulley 494 about its axis may be controlled manually (e.g., by an operator-controlled knob) and/or by motor 450. In an exemplary embodiment where crimp 492 is attached to sliding portion 490, movement of sliding portion 490 in the proximal direction may move the side of snare device 416 that is on the same side as crimp 492 toward pulley 494 (e.g., proximally) and rotate snare device 416 and pulley 494 counterclockwise. Movement of sliding portion 490 in the distal direction may move the side of snare device 416 that is on the same side as crimp 492 away from pulley 494 (e.g., distally) and rotate snare device 416 and pulley 494 clockwise. Where crimp 492 is not attached to sliding portion 490, pulley 494 and snare device 416 may be rotated by a knob (not shown) and/or motor 450. In an exemplary embodiment where crimp 492 is free of sliding portion 490, pulley 494 and/or snare device 416 may be rotated by a knob (not shown) and/or by motor 450. Pulley 494 may be rotatably suspended on an extension of sliding portion 490, such that movement of sliding portion 490 may be used to extend and retract the loop, while the knob and/or motor 450 may rotate pulley 494 and snare device 416. In some examples, snare device 416 may include teeth 440 on at least a portion (e.g., the portion configured to surround the tissue/the distal loop) of its inner surface. In such examples, the pulley 494 and/or motor 450 may be configured to pull the snare device 416 back and forth (e.g., alternating between clockwise and counterclockwise), creating a sawing motion and cutting through the tissue. In some examples, snare device 416 may include teeth 440 over the entire interior-facing surface of the snare device 416. In such examples, pulley 494 may include a gear with teeth that mesh with teeth 440. In examples in which the teeth cover the entire interior of snare device 416, the pulley 494 and/or motor 450 may be configured to alternate between clockwise and counterclockwise rotation and/or continually rotate in the same direction. As shown in FIG. 4, rotating pulley 494 in the clockwise direction, likewise rotates the distal end (e.g. the distal loop) of snare device 416 in clockwise direction. As snare device 416 saws through the target tissue, sliding portion 490 may be moved proximally to move snare device 416 proximally and continue to saw previously un-sawed portions of the target tissue.

Figure 4A:
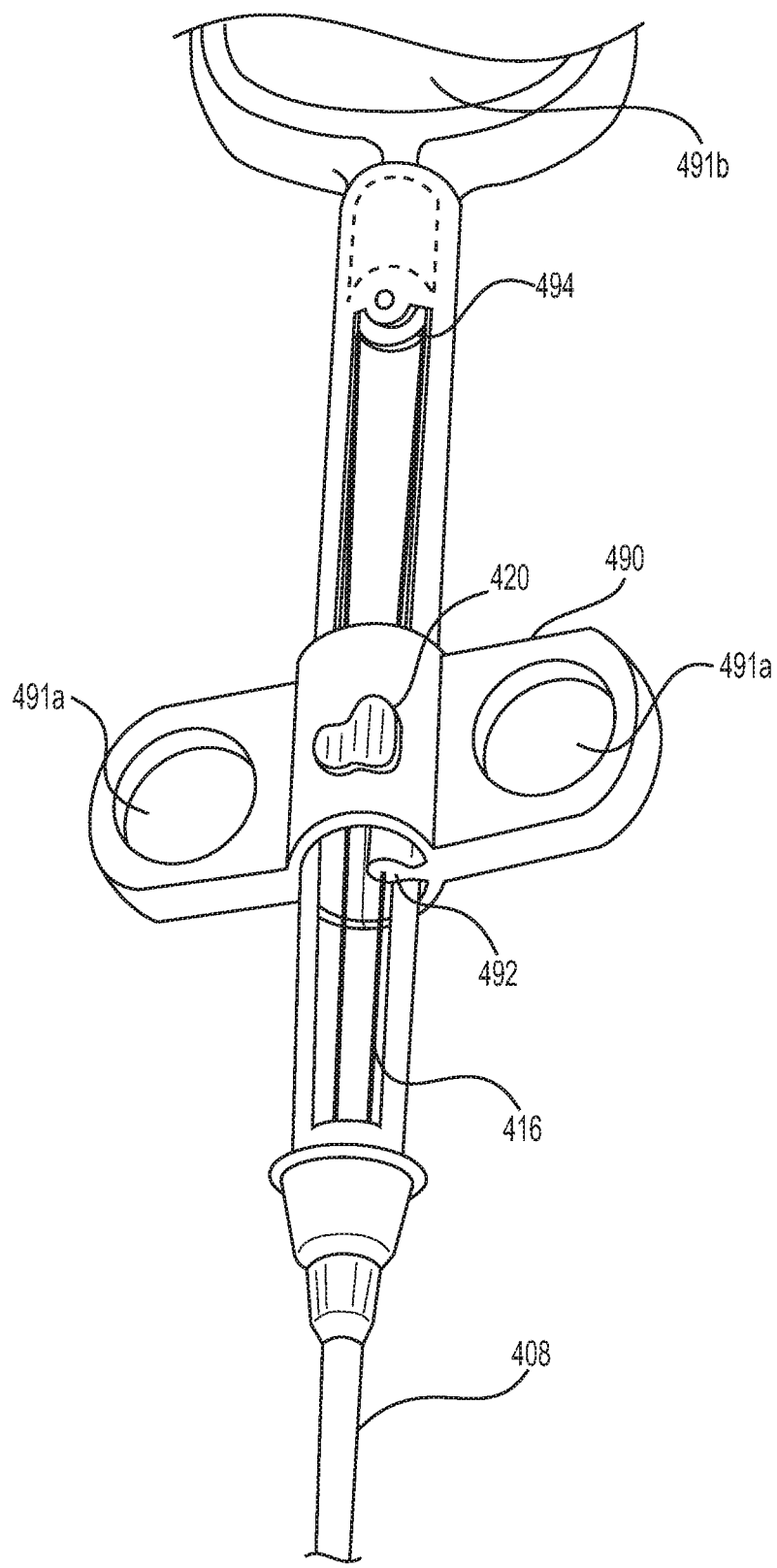
FIG. 4A illustrates a front perspective view of the alternative exemplary medical device of FIG. 1.

FIG. 4A illustrates a perspective view of the exemplary handle of FIG. 4. As shown in FIG. 4A, the handle may include button 420. In some examples, snare device 416 may be in the form of a loop and one segment of the loop may be fixedly attached to sliding portion 490 by crimp 492. When button 420 is not engaged, sliding portion 490 may be moved proximally to move snare device 416 around pulley 494 and in a counterclockwise direction, and, conversely, sliding portion 490 may be moved distally to move snare device 416 in a clockwise direction. When button 420 is engaged, by, for example, an operator holding button 420 down, a second segment of the loop may be cinched. For example, the depressed button 420 may press the second segment of the loop against an interior surface of the handle, thus frictionally securing the second segment between button 420 and the interior surface. Engaging button 420 may also initiate a friction lock device (not shown) to hold the second segment in place. When button 420 is engaged, the loop may not circulate, and thus, moving sliding portion 490 proximally may draw snare device 416 and/or distal loop in the proximal direction and tighten the distal loop around a base region or neck of target tissue. Further, when button 420 is engaged, moving sliding portion 490 distally may move snare device 416 and/or the distal loop in the distal direction to extend the loop around target tissue.

V. Alternative Actuation Mechanism

Figure 5:
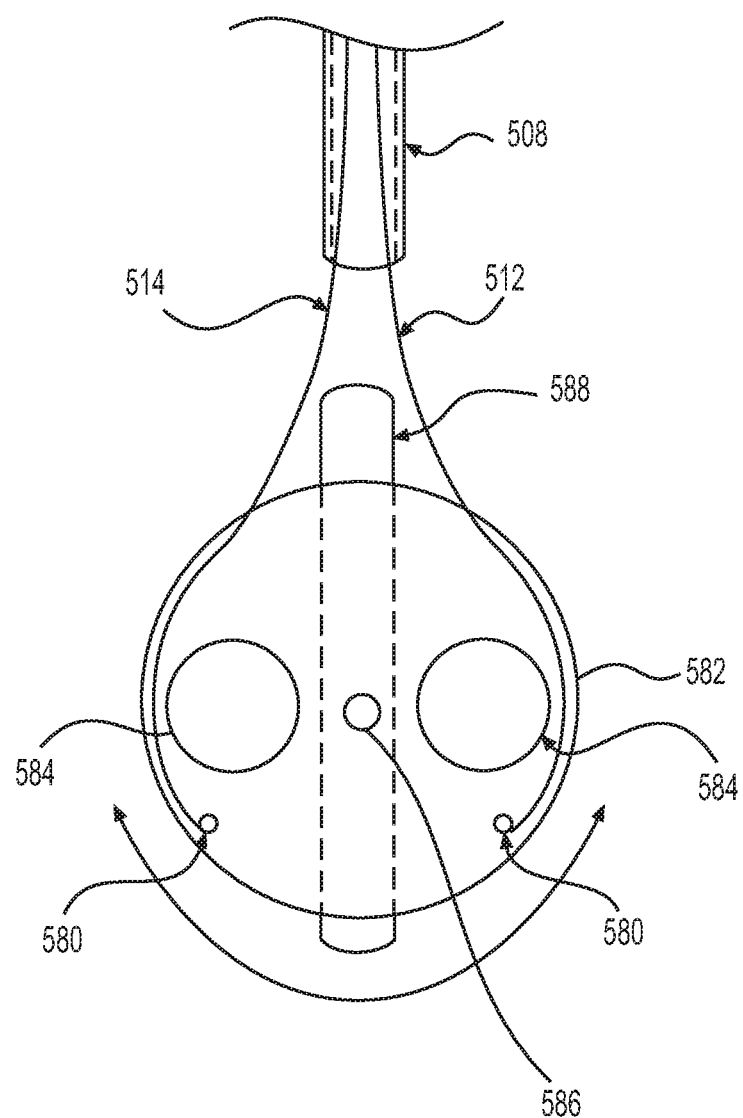
FIG. 5 illustrates an exemplary actuation mechanism, according to the present disclosure.

FIG. 5 illustrates an alternative actuation mechanism, including a rotatable handle portion, e.g., rotation wheel 582. Rotation wheel 582 may be mounted on a handle of a medical device (e.g., handle 110 of device 100 and/or handle 410 of device 400). The proximal ends of side/leg 514 of a snare device and side/leg 512 of the snare device may extend proximally of a proximal end of a sheath 508. The proximalmost ends of sides 512 and 514 of the snare device may attach to wire attachments 580 of rotation wheel 582. Rotation wheel 582 may include two finger holes 584 for the operator's fingers. Rotation wheel 582 may be rotatably attached to a slide slot 588 within the handle. Slide slot 588 allows the distal end (not shown) of the snare device to open and close by moving rotation wheel 582 distally and proximally within slot 588. By moving rotation wheel 582 clockwise and counterclockwise, the distal end of the snare device will rotate clockwise and counterclockwise, respectively. If the distal end of the snare device is looped around tissue, alternating clockwise and counterclockwise movement may saw through the tissue. Thus, the configuration illustrated in FIG. 5 allows a distal end of a snare device to reciprocate while opening and closing.

VI. Alternative Actuation Mechanisms for Independent Control

Figure 6:
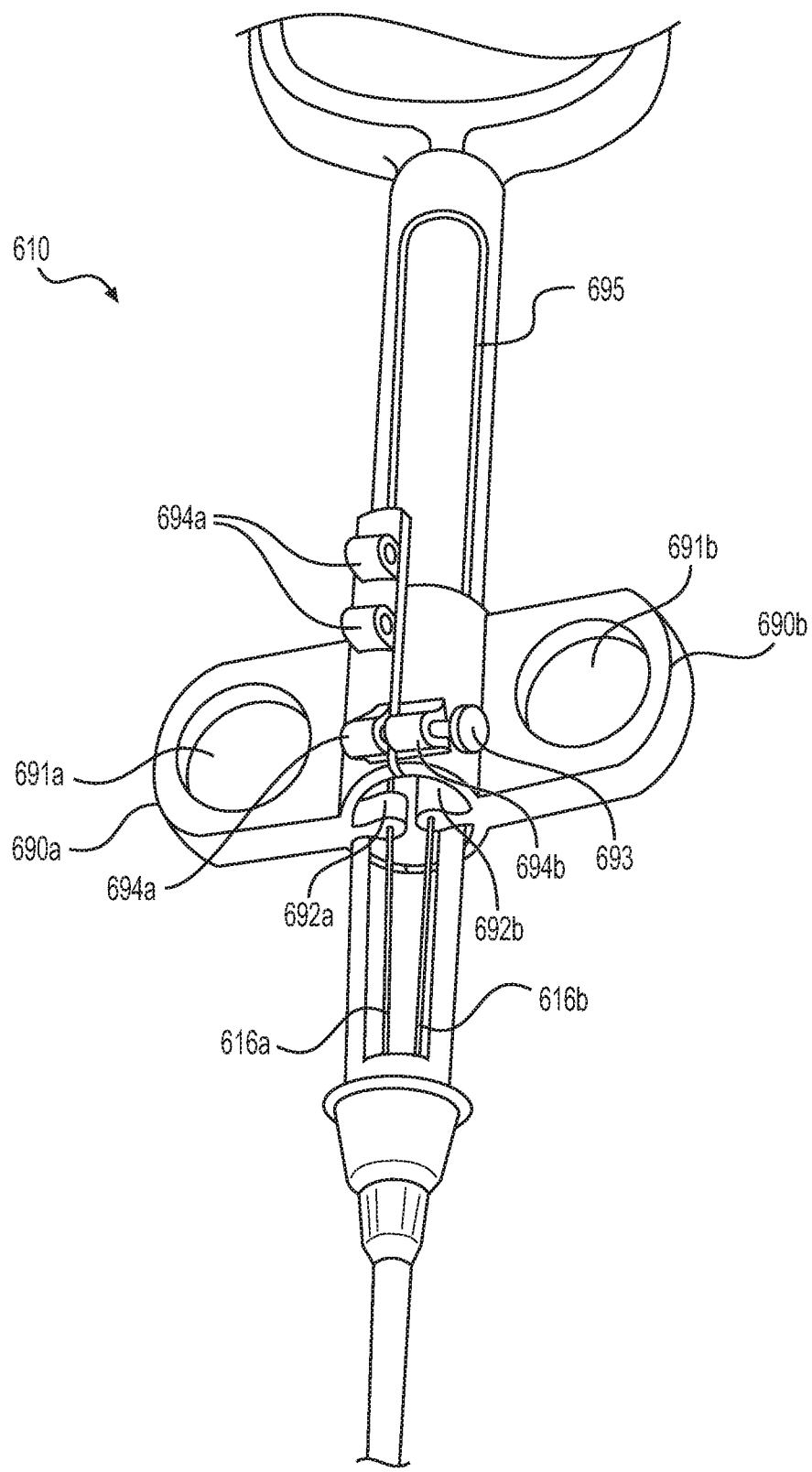
FIG. 6 illustrates an exemplary handle for a medical device, according to the present disclosure.

As discussed above, exemplary medical devices disclosed herein may allow an operator to manipulate proximal ends of the snare legs independently from each other. FIGS. 6, 7A, 7B, and 7C depict exemplary medical device handles that allow an operator to independently control the proximal ends of the snare legs. In the device of FIG. 6, handle 610 may be similar in some aspects to the handle shown in FIG. 4A, but the handle of FIG. 6 is designed to allow the proximal region of snare leg 616a to be manipulated independently from the proximal region of snare leg 616b. By allowing independent control of the different snare legs at the proximal region, the operator may thus be able to change the configuration of the snare loop formed at the distal end.

Crimps 692a and 692b of handle 610 may attach to the proximal regions of snare legs 616a and 616b, respectively. Handle 610 may also include a sliding portion that is separated into two separate pieces—sliding portion 690a and sliding portion 690b—which may be controlled independently of one another. Crimp 692a may connect a proximal region of snare leg 616a to sliding portion 690a, and crimp 692b may connect a proximal region snare leg 616b to sliding portion 690b, so that movement of sliding portions 690a and 690b move snare legs 616a and 616b, respectively. As a result, snare legs 616a and 616b may be moved independent of one another.

Handle 610 may include a rotatable handle portion, e.g., pulley 695, as described in reference to pulley 494 of handle 410. The proximal end of snare device 616 may loop around pulley 695, and snare device 616 may ride over pulley 695. In the exemplary embodiment of FIG. 6, crimp 692a is attached to sliding portion 690a, and movement of sliding portion 690a in a proximal direction may move snare leg 616a toward pulley 695 (e.g., proximally) and rotate snare device 616 and pulley 695 clockwise, which may move sliding portion 690b, crimp 692b, and snare leg 616b in a distal direction, away from pulley 695. Movement of sliding portion 690a in a distal direction may move snare leg 616a and crimp 692a away from pulley 695 (e.g., distally) and rotate snare device 616 and pulley 695 counterclockwise, which may move sliding portion 690b, crimp 692b, and snare leg 616b in a proximal direction, towards pulley 695. Movement of sliding portion 690b may also affect the movement of sliding portion 690a in a similar manner, with movement of 690b in a proximal direction causing movement of 690a in a distal direction, and vice versa.

Pushing sliding portion 690a in a distal direction may move a proximal region of snare leg 616a further distally, extending a distal region of snare leg 616a further out of a distal end of a sheath (not shown), and pulling sliding portion 690a in a proximal direction may withdraw snare leg 616a further within the sheath. Pushing sliding portion 690b in a distal direction may cause a proximal region of snare leg 616b to move further distally, extending a distal region of snare leg 616b further out of a distal end of the sheath, and pulling sliding portion 690b in a proximal direction may withdraw snare leg 616b further within the sheath. In this way, having two separate sliding portions 690a and 690b may allow an operator to position sliding portions 690a and 690b in different orientations relative to each other to change the configuration of the snare loop at the distal end of the snare device. As is shown in FIGS. 3A-3D, relative positioning of the snare legs may alter the configuration of the snare loop at the distal end. Handle 610 may allow an operator to independently control the positioning of a proximal region of the snare legs to achieve different snare loop configurations at the distal end. To assist an operator with positioning sliding portions 690a and 690b relative to each other to achieve the desired configuration of snare loop at the distal end, handle 610 may also include one or more indicators to signal to the operator how to orient the sliding portions relative to one another in order to achieve different configurations, as described in further detail below.

Handle 610 may also optionally allow an operator to lock sliding portion 690a relative to sliding portion 690b to allow the operator to optionally fix the relative positions of sliding portions 690a and 690b to manipulate both sliding members 690a and 690b together as a single unit, for example, once the desired configuration of snare loop at the distal end has been achieved. Sliding portion 690b may include finger hole 691b and a male locking member 694b. In FIG. 6, male locking member 694b includes a slidable pin 693. Sliding portion 690a may include a finger hole 691a and a plurality of female locking members 694a, which comprise openings in the exemplary handle of FIG. 6. Sliding portions 690a and 690b may be slid proximally and distally relative to one another to position pin 693 into alignment with any of female locking members 694a. Once aligned with the chosen female locking member, pin 693 may be moved towards the female locking member 694a to engage pin 693 with an opening of female locking member 694a. To disengage a female locking member 694, pin 693 may be slid away from the female locking member 694a to disengage pin 693 from the opening. In this way, pin 693 may be moved into or out of engagement with any one of female locking members 694a.

When pin 693 is not engaged with a female locking member 694a, sliding portions 690a and 690b may slide independently of one another. However, when pin 693 is engaged with a female locking member 694a, sliding portion 690a may be locked in position relative to sliding portion 690b, and thus moving sliding portion 690a may cause synchronous movement of 690b, and vice versa. Depending on how sliding portions 690a and 690b are positioned relative to one another when locked, finger holes 691a and 691b may be offset from each other during this synchronous movement. In this way, handle 610 may allow movement of each sliding portion 690a and 690b to be manipulated independently of each other or to be synchronized together with one another as one single unit. As a result, proximal regions of snare legs 616a and 616b may be moved independently of one another when sliding portions 690a and 690b are disengaged from one another or to be moved together when sliding portions 690a and 690b are locked with one another via female and male locking members 694a and 694b.

Although FIG. 6 shows three female locking members 694a, handle 610 may include one, two, or more than three female locking members 694a. Further, female locking members 694a may be spaced evenly apart from one another, or they may be spaced from one another at uneven intervals. It will also be understood that although a pin-and-aperture locking mechanism is shown in FIG. 6, any suitable locking mechanism, e.g., a screw/twist-fit, friction-fit, snap-fit, magnetic coupling, lever lock, ratchet, or other mechanism may be used instead of, or in addition to, the pin and aperture locking mechanism of FIG. 6. Depending on the type of locking mechanism used, female locking members 694a may include one or more apertures, ridges, recesses, protrusions, threaded portions, etc. to accommodate the type of locking mechanism employed.

During use, an operator may move sliding portions 690a and 690b independently of one another in order to manipulate the size and/or shape of a distal loop of the snare, e.g., as shown in FIGS. 3A-3D. In some aspects, female locking members 694a may be spaced apart from one another so as to provide a number of optional pre-set snare types at the distal end of the snare. For example, locking sliding portion 690b relative to sliding portion 690a to engage pin 693 with a specific female locking member 694a may move snare legs 616a and 616b relative to one another to form a specific configuration of snare loop at the distal end. To aid in positioning of the sliding portions and control of the distal snare configuration, handle 610 may also include one or more indicators to signal to the operator which female locking members 694a allow the operator to achieve which configuration of snare loop at the distal end. One or more visual indicators may be included to identify what the snare loop looks like at the distal end of the device when sliding portions 690a and 690b are locked relative to one another in a certain position. For example, each female locking member 694a may be color-coded, numbered, lettered, etc., or one or both of sliding portions 690a or 690b may include one or more visual indicators (e.g., images, words, letters, numbers, colors, symbols, etc.) to indicate to the operator how sliding portions 690a and 690b may be locked relative to one another to achieve a certain desired type of snare loop a the distal end.

Once the operator achieves the desired loop shape and/or size by positioning sliding portions 690a and 690b relative to one another, the operator may then lock sliding portions 690a and 690b together to maintain the relative positioning. Once sliding portions 690a and 690b are locked relative to one another, the operator may move sliding portions 690a and 690b as a single unit distally and/or proximally to open and/or close the distal snare loop while maintaining the positioning of snare leg 616a relative to snare leg 616b. Snare device 616 may be configured so that when sliding portions 690a and 690b of handle 610 are slid in a distal direction, a portion of snare device 616 extends distally from a sheath. When sliding portions 690a and 690b are slid in a proximal direction, snare device 616 may be withdrawn and may be substantially collapsed and disposed within the sheath.

In this way, handle 610 may allow an operator to push and/or pull each side of the snare independently to achieve different snare loop sizes and/or shapes, while also having the option to jointly move both sides of the snare, e.g., to open or close the snare without losing the chosen snare configuration, when sliding portions 690a and 690b are locked relative to one another. It will be recognized that, depending on how sliding portions 690a and 690b are locked relative to one another, finger openings 691a and 691b may be offset from one another when opening and/or closing the snare.

Figure 7A:
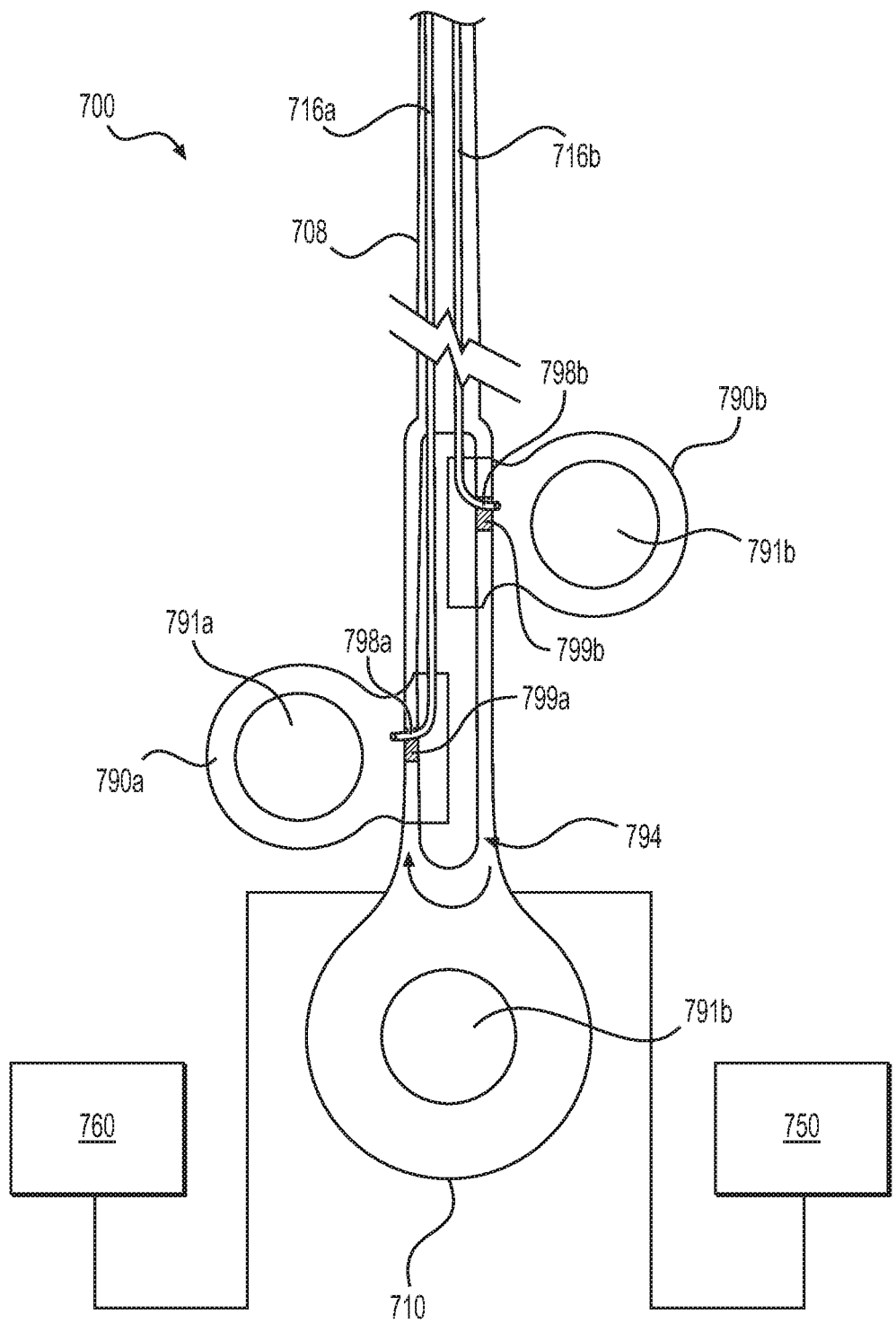
FIG. 7A illustrates another exemplary handle for a medical device, according to the present disclosure.

FIG. 7A depicts a medical device handle 700 that also allows for independent manipulation of snare legs 716a and 716b. Handle 700 of FIG. 7A may be similar in some aspects to that of FIG. 4, but with separate sliding portions 790a and 790b, similar to FIG. 6.

Like FIG. 4, handle 700 may be controlled manually and/or by a motor 750 and may be operably connected to an electrical source 760, allowing use with motor 750 and/or allowing snare device 716 to be used for electrocautery, etc.

Like FIG. 6, sliding portions 790a and 790b may be connected to proximal regions of snare legs 716a and 716b, respectively, allowing independent manipulation of snare legs 716a and 716b as sliding portion 790a and sliding portion 790b are moved distally and proximally relative to one another. An end 798a of a proximal region of snare leg 716a may be coupled with sliding portion 790a, and an end 798b of a proximal region of snare leg 716b may be coupled with sliding portion 790b. Sliding portions 790a and 790b may then be coupled to a pulley 794, which may operate similarly to pulleys 494 and 695 of FIGS. 4A and 6, respectively. For example, the proximal ends of snare device 716 may be connected via sliding portions 790a and 790b to a loop that wraps around pulley 794. Movement of sliding portion 790a in a proximal direction may move snare leg 716a toward pulley 794 (e.g., proximally) and rotate snare device 716 and pulley 794 counterclockwise, which may move sliding portion 790b and snare leg 716b in a distal direction, away from pulley 794. Movement of sliding portion 790a in the distal direction may move snare leg 716a away from pulley 794 (e.g., distally) and rotate snare device 716 and pulley 794 clockwise, which may move sliding portion 790b and snare leg 716b in a proximal direction, towards pulley 794. Movement of sliding portion 790b may also affect the movement of sliding portion 790a in a similar manner, with movement of 790b in a proximal direction causing movement of 790a in a distal direction, and vice versa.

Pushing sliding portion 790a in a distal direction may move a proximal region of snare leg 716a further distally, extending a distal region of snare leg 716a further out of a distal end of a sheath (not shown), and pulling sliding portion 790a in a proximal direction may withdraw snare leg 716a further within the sheath. Pushing sliding portion 790b in a distal direction may cause a proximal region of snare leg 716b to move further distally, extending a distal region of snare leg 716b further out of a distal end of the sheath, and pulling sliding portion 790b in a proximal direction may withdraw snare leg 716b further within the sheath. In this way, having two separate sliding portions 790a and 790b may allow an operator to position sliding portions 790a and 790b in different orientations relative to each other to change the configuration of the snare loop at the distal end of the snare device. As is shown in FIGS. 3A-3D, relative positioning of the snare legs may alter the configuration of the snare loop at the distal end. Handle 700 may allow an operator to independently control the positioning of a proximal region of the snare legs to achieve different snare loop configurations at the distal end. To assist an operator with positioning sliding portions 790a and 790b to achieve the desired configuration of snare loop at the distal end, handle 700 may also include one or more indicators 799a or 799b to signal to the operator how to orient the sliding portions relative to one another in order to achieve different configurations, as described in further detail in reference to handle 610. Handle 700 may also include a locking mechanism for locking the relative position of sliding portions 790a and 790b in place relative to each other—similar to handle 610—or handle 700 may not include any locking mechanisms. Use of handle 700 and snare 716 may be similar to the use of handle 610 described in reference to FIG. 6.

In some embodiments, handle 700 may be configured to allow an operator to manipulate snare legs 716a and 716 independently of each other, without necessarily moving the other snare leg. In such embodiments, moving sliding portion 790a and thus snare leg 716a may not necessarily cause movement of sliding portion 790b and snare leg 716b, and vice versa. To achieve this type of independent movement, pulley 794 may be operably connected to a spring (not shown). The inclusion of a spring in the pulley system may allow pulley 794 to move proximally and distally to take up extra slack as each snare leg 716a and 716b is moved proximally and distally. By allowing pulley 794 to move proximally or distally as each snare leg 716a and 716b is moved may allow an operator to move one snare leg without necessarily moving the other snare leg. For example, sliding portion 790a may be moved proximally, towards pulley 794, and pulley 794 connected to a spring may also move proximally as slack is introduced into the system instead of directly causing movement of sliding portion 790a in a distal direction. Additionally or alternatively, in some embodiments, there may be additional slack built into the pulley system at the proximal end, so that movement of one snare leg does not necessarily translate into a 1:1 ratio of movement of the other snare leg in the opposite direction.

Figure 7B:
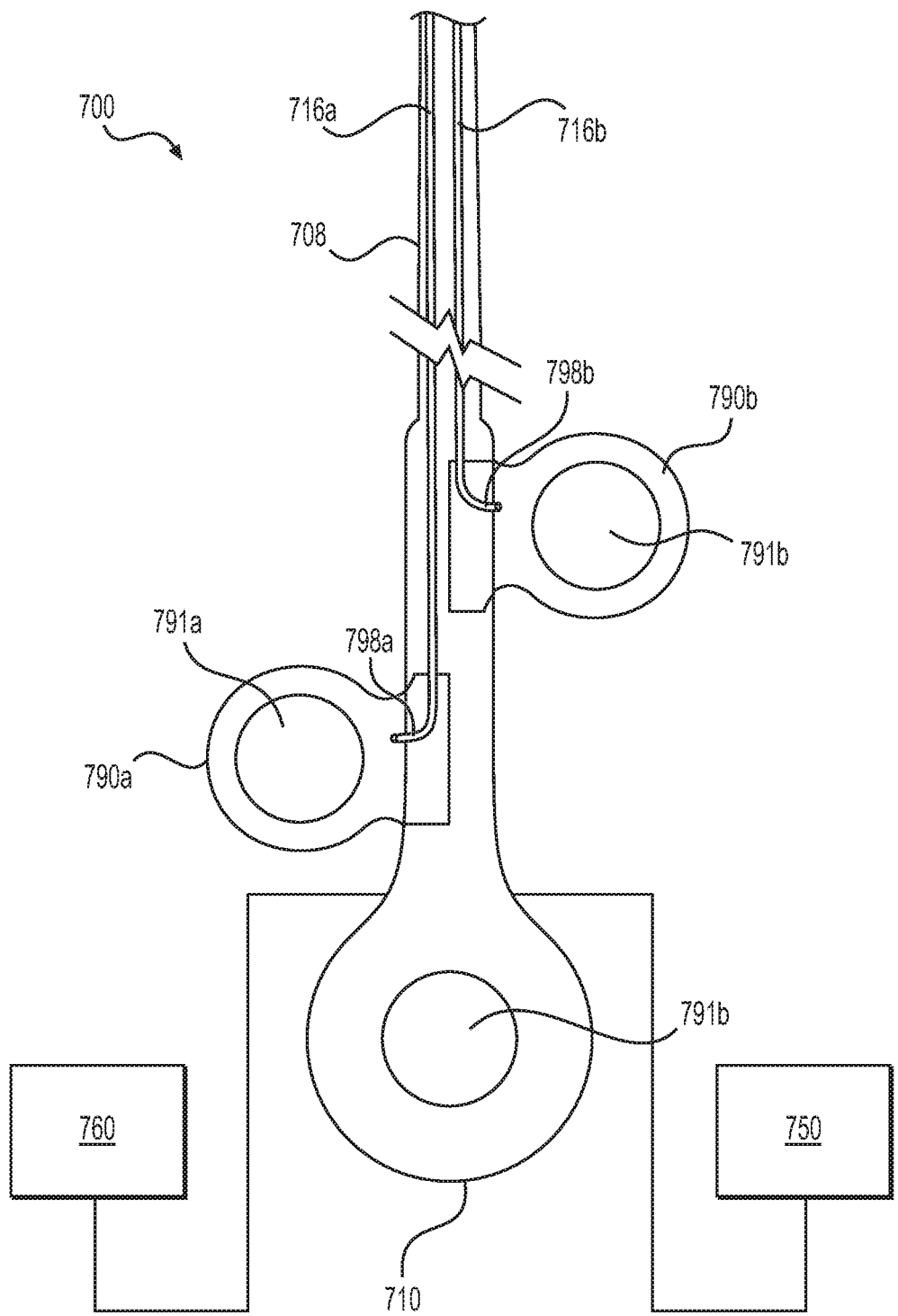
FIG. 7B illustrates yet another exemplary handle for a medical device, according to the present disclosure.

FIG. 7B depicts an alternative embodiment of handle 700 configured to allow an operator to manipulate snare legs 716a and 716b independently of each other, without necessarily moving the other snare leg. Instead of proximal regions of snare legs 716a and 716b being connected with one another to form a continuous loop with a pulley 794, as in the embodiment of FIG. 7A, in the embodiment of FIG. 7B, the proximal ends of the snare device may be free and operably disconnected from one another. For example, as shown in FIG. 7B, a proximal end 798a of snare leg 716a couples to sliding portion 790a, and a proximal end 798b of snare leg 716b couples to sliding portion 790b, without any direct connections movably coupling sliding portion 790a to sliding portion 790b. Because snare legs 716a and 716b and sliding portions 790a and 790b are not coupled to each other at a proximal region, movement of one sliding portion does not affect movement of the other sliding portion. Handle 700 of FIG. 7B may operate similarly to handle 700 of FIG. 7A and handle 610 of FIG. 6, except that—like the spring embodiment—the movement of sliding portions 790a and 790b may not be linked.

Figure 7C:
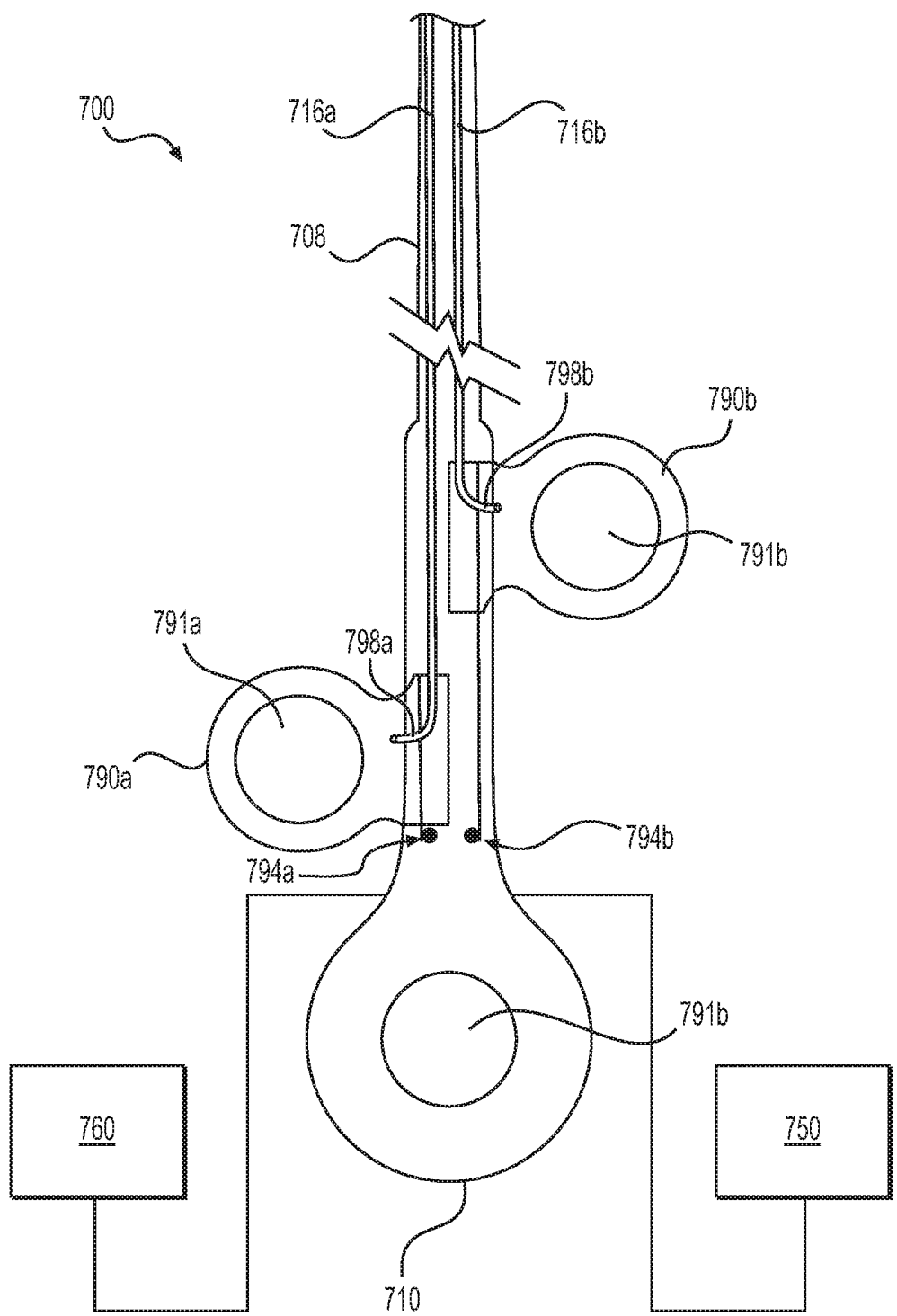
FIG. 7C illustrates yet another exemplary handle for a medical device, according to the present disclosure.

The embodiment of FIG. 7C also depicts a handle 700 having proximal ends of the snare device that are free and operably disconnected from one another, as in FIG. 7B. In FIG. 7C, rather than a loop coupling sliding portions 790a and 790b to a common pulley, as in FIG. 7A, each sliding portion 790a and 790b may be coupled to its own cable that wraps around its own individual spool. Snare leg 716a may be coupled to sliding portion 790a, which is connected by a cable to spool 794a, and snare leg 716b may be coupled to sliding portion 790b, which is connected by a cable to spool 794b. By coupling the snare legs and their respective sliding portions to their own individual spool, the sliding portions and snare legs may be controlled separately from one another at the proximal and distal ends, with movement of one sliding portion not necessarily causing any movement in the other sliding portion. For example, spools 794a and 794b may be biased into a wrapped configuration so that as sliding portion 790a or sliding portion 790b, respectfully, is moved proximally, the corresponding cable may wrap around the corresponding spool to take up the slack. As sliding portion 790a or sliding portion 790b is moved distally, the corresponding cable may unwind from the corresponding spool to take up provide more slack. Spools 794a and 794b may be spring-biased. For example, spool 794a may be urged to rotate in a counterclockwise direction by spring-biasing, and/or spool 794b may be urged to rotate in a clockwise direction by spring-biasing. This may assist with winding the cables around spool 794a and/or spool 794b.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A medical device, comprising:
   a handle portion;
   a rotatable body mounted to the handle portion, wherein a center of the rotatable body is aligned with a longitudinal axis of the handle portion, wherein the rotatable body includes two finger holes, wherein a first of the two finger holes is positioned on a first side of the longitudinal axis, and wherein a second of the two finger holes is positioned on a second, opposite side of the longitudinal axis; and
   only one distal loop of a continuous wire, the only one loop having:
      a first leg having a proximal end coupled to the rotatable body; and
      a second leg having a proximal end coupled to the rotatable body, wherein rotation of the rotatable body causes the proximal end of the first leg to move distally and, simultaneously, the proximal end of the second leg to move proximally, wherein the first of the two finger holes is between the proximal end of the first leg and the longitudinal axis, and wherein the second of the two finger holes is between the proximal end of the second leg and the longitudinal axis.

2. The medical device of claim 1, wherein the rotatable body is configured to be contacted and manipulated by a hand of a user so as to cause rotation of the rotatable body.

3. The medical device of claim 2, wherein the rotation of the rotatable body is about an axis transverse to the longitudinal axis of the handle portion.

4. The medical device of claim 1, wherein the handle portion includes a slot, and wherein the rotatable body is rotatably mounted in the slot.

5. The medical device of claim 4, wherein the rotatable body is longitudinally movable in at least one of a proximal or distal direction within the slot.

6. The medical device of claim 5, wherein longitudinal movement of the rotatable body causes the distal loop to at least one of open or close.

7. The medical device of claim 4, wherein the slot extends both distally and proximally past each of the first and second finger holes.

8. The medical device of claim 4, wherein a length of the slot along a longitudinal direction of the device is larger than a diameter of the rotatable body.

9. The medical device of claim 1, wherein the proximal end of the first leg is attached to a first wire attachment of the rotatable body, and wherein the proximal end of the second leg is attached to a second wire attachment of the rotatable body, and wherein each of the first and second wire attachments is more proximal than a proximalmost point of each of the first and second finger holes.

10. The medical device of claim 1, wherein the only one loop lies in a plane.

11. A medical device, comprising:
a body that is configured to be rotatably and longitudinally movable relative to a handle portion of the device, the body having two finger holes; and
only one distal loop, the only one loop lying in a plane and having:
a first leg having a proximal end coupled to the body; and
a second leg having a proximal end coupled to the body, wherein the first leg and the second leg form the distal loop, wherein the proximal end of the first leg and the proximal end of the second leg are proximal to each of the two finger holes of the body, wherein a first of the two finger holes is between the proximal end of the first leg and the longitudinal axis of the handle portion, and wherein a second of the two finger holes is between the proximal end of the second leg and the longitudinal axis.

12. The medical device of claim 11, wherein the body is configured to be contacted and manipulated by a hand of a user so as to cause rotation of the body.

13. The medical device of claim 11, wherein rotation of the body causes rotation of the distal loop, and wherein longitudinal movement of the body causes the distal loop to at least one of open or close.

14. The medical device of claim 11, wherein the handle portion includes a slot, and wherein the body is mounted in the slot.

15. The medical device of claim 14, wherein the rotation of the body is about an axis transverse to a longitudinal axis of the slot.

16. The medical device of claim 14, wherein a length of the slot along a longitudinal direction of the device is larger than a diameter of the body.

17. A medical device, comprising:
a handle portion;
a body mounted in a slot of the handle portion such that the body is configured to be rotatably and longitudinally movable relative to the handle portion, wherein a center of the body is aligned with a longitudinal axis of the slot, wherein the body includes two finger holes, wherein a first of the two finger holes is positioned on a first side of the longitudinal axis, and wherein a second of the two finger holes is positioned on a second, opposite side of the longitudinal axis; and
only one distal loop of a continuous wire, the only one loop having:
a first leg having a proximal end coupled to the body, wherein the proximal end of the first leg is proximal to the first of the two finger holes, and wherein the first of the two finger holes is between the proximal end of the first leg and the longitudinal axis; and
a second leg having a proximal end coupled to the body, wherein the proximal end of the second leg is proximal to the second of the two finger holes, and wherein the second of the two finger holes is between the proximal end of the second leg and the longitudinal axis.

18. The medical device of claim 17, wherein a distal end of the first leg and a distal end of the second leg form the distal loop, wherein rotation of the body causes rotation of the distal loop, and wherein longitudinal movement of the body causes the distal loop to at least one of open or close.

19. The medical device of claim 17, wherein the rotation of the body is about an axis transverse to the longitudinal axis of the slot.

20. The medical device of claim 17, wherein the only one loop lies in a plane.

* * * * *